US005387220A

United States Patent [19]
Pisharodi

[11] Patent Number: 5,387,220
[45] Date of Patent: Feb. 7, 1995

[54] STEREOTACTIC FRAME AND LOCALIZATION METHOD

[76] Inventor: Maohaven Pisharodi, 942 Wild Rose La., Brownsville, Tex. 78520

[21] Appl. No.: 77,026

[22] Filed: Jun. 15, 1993

[51] Int. Cl.[6] .......................................... A61B 19/00
[52] U.S. Cl. .................................. 606/130; 128/898
[58] Field of Search ............... 128/898; 606/1, 130; 604/116

[56] References Cited

U.S. PATENT DOCUMENTS

| | | | |
|---|---|---|---|
| 3,841,148 | 10/1974 | Becker | 606/130 |
| 4,256,112 | 3/1981 | Kopf et al. | 606/130 |
| 4,465,069 | 8/1984 | Barbier et al. | 606/130 |
| 5,263,494 | 11/1993 | Margelos et al. | 606/130 |

FOREIGN PATENT DOCUMENTS 2213066  8/1989  United Kingdom ................ 606/130

*Primary Examiner*—Stephen C. Pellegrino
*Assistant Examiner*—Glenn Dawson
*Attorney, Agent, or Firm*—Gunn, Lee & Miller

[57] ABSTRACT

Applicant's invention is a stereotactic frame and localization method incorporating localization frames which is operable without the use of head pins or screws. Initially, using the localization frames, natural reference points, lines, and planes are established and aligned in relation to a patient's head. These natural references provide cranial landmarks for proper attachment and alignment of the stereotactic frame. This stereotactic frame includes a means for positioning and locking the frame as well a multiplicity of adjustable elements which are adjusted according to the determined values of the variables such that localization of a target point within a patient's head is possible.

31 Claims, 6 Drawing Sheets

STEREOTACTIC FRAME AND LOCALIZATION METHOD

FIELD OF THE INVENTION

This invention pertains to a stereotactic frame and localization method utilized during stereotactic neurosurgery, and more particularly to a stereotactic frame and localization method for use during stereotactic surgery which utilize natural reference points and do not require head pins.

BACKGROUND INFORMATION

The general theory of stereotactic neurosurgery is that if an arc is formed alongside the patient's head any trajectory passing through this arc at a right angle to the arc will always meet at the central point of the arc. Employment of this theory enables localization of any point within the head. However, when examining present stereotactic equipment, the most striking feature is that in spite of tremendous advancement in scanning techniques and the effective arc principle, the present stereotactic frames are very complicated and difficult to maneuver.

Most of the present equipment requires fixation of the stereotactic frame to the patient's head before scanning is performed. Screws or head pins are used to secure the stereotactic frame to the patient's head. Since the frame must be left on the patient's head from the time of scanning until the time of the surgery, the scanning must be done the morning of the surgery. This naturally delays the neurosurgical procedure. In practical terms, every stereotactic procedure will take about three (3) to four (4) hours of a neurosurgeon's morning because of this inconvenience.

In addition, when using stereotactic devices which require pinning the whole frame to the patient's head it is extremely difficult to localize lesions of the posterior fossa. Localizing lesions of the posterior fossa requires the neurosurgeon to reverse the whole frame. This is an extremely cumbersome procedure and very often is not practical.

There is a need for a stereotactic frame and localization method which utilizes naturally occurring cranial reference points which can be accurately and consistently reproduced when the stereotactic frame is secured to the patient's head at the time of surgery. Applicant's invention meets this need since it enables scanning anytime before surgery without securing the whole stereotactic frame to the patient's head and allows for accurate and consistent reproduction of the cranial reference points at the time of surgery.

BRIEF SUMMARY OF THE INVENTION

Applicant's invention addresses the need for a stereotactic frame and localization method which is operable without the use of head pins or screws and which can be done anytime before surgery. Applicant describes a localization method which comprises the steps of initially establishing several natural cranial reference points. Once the natural reference points are established, localization proceeds. Applicant's invention utilizes a spherical coordinate system incorporating lines, planes and angles referenced on and within the head. Applicant's invention includes localization frames which work in conjunction with this spherical coordinate system by establishing an orbitomeatal line on each side of the head which then serves as the initial cranial reference for orientation of the remaining lines, planes and angles. X-ray beams are used to verify proper alignment of the localization frames and consequently the other cranial references. Once alignment is verified and x-rays are taken, variable values are determined with respect to the pre-established references and the target point within the head.

The stereotactic Frame is then attached to the head frame wherein the components of the stereotactic frame are adjusted and secured in relation to the variable values. Specifically, a first disc is aligned with an orbitomeatal and vertical plane. A second and third disc are attached to the end of an elongated rod which slidably engages the first disc. This second and third disc are slid towards the first disc such that the second disc is immediately adjacent to the first disc. In addition, a radial arm with slidably attached arc is attached to the rotatable third disc. The three discs, radial arm, and arc are now adjusted and manuevered distances and angles correlating to the variable values. A needle guide passing through this arc meets the target point at the central point of the arc physically localizing the target point within the patient's head.

It is an object of Applicant's invention to provide a stereotactic localization system which utilizes the sphere principle.

It is a further object of Applicant's invention to provide a stereotactic frame and localization method which avoids use of a stereotactic frame which must be pinned to the patient's head for the purpose of making scans and subsequently for the purpose of localization during the surgery.

It is a further object of Applicant's invention to provide a stereotactic frame and localization method which, by incorporating variables which are taken with reference to already available cranial landmarks, permit stereotactic localization and surgery without the use of head pins.

It is a further object of Applicant's invention to provide a stereotactic frame and localization method which employs localization frames to establish and align cranial landmarks.

It is a further object of Applicant's invention to provide a stereotactic frame and localization method which allows localization of a point in the brain between the external auditory meatii in any plane related to an orbitomeatal plane and a vertical plane, pre-established planes created with reference to cranial landmarks.

It is a further object of Applicant's invention to provide a stereotactic frame which, by incorporation of a snake-like retractor arm, permits positioning of the stereotactic frame in any position which may be essential for a particular type of surgery.

It is a further object of Applicant's invention to provide a stereotactic frame which can be moved away from the patient's head and the surgery field and accurately returned.

It is a further object of Applicant's invention to provide a stereotactic frame which can be adapted for use with any head-holding frame or device.

It is a further object of Applicant's invention to provide a stereotactic frame and localization system which is MRI compatible.

DETAILED DESCRIPTION

Applicant describes a stereotactic frame (10) and localization method for stereotactic localization which avoids pinning the frame to the patient's head (11) for the purpose of scanning and subsequent localization during surgery. Applicant's method utilizes existing cranial landmarks on and in a patient's head (11) which can be accurately and consistently referenced again-and again. By making reference to these points at the time of scanning and later at the time of surgery, the stereotactic frame can be removed from the surgery field and the patient's head (11) as necessary.

Figure 1:
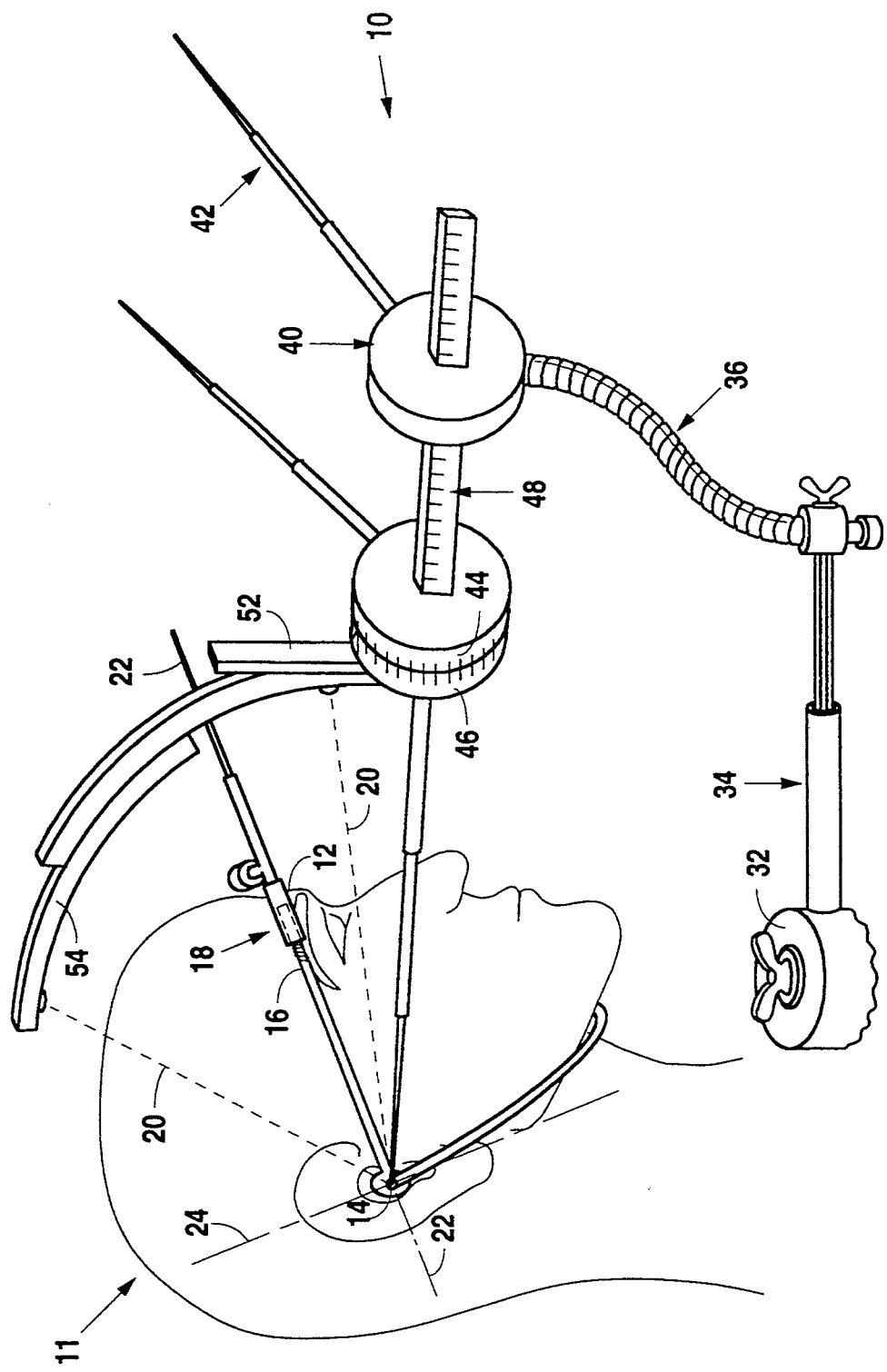
FIG. 1 is a rear perspective view of Applicant's invention including the stereotactic frame and the cranial reference planes for Applicant's localization method.

Referring to FIG. 1, Applicant's invention takes advantage of the fact that a line drawn from the upper margin of the eye or orbital ridge (12) to the mid-point of the ear or external auditory meatus (14) is a constant line for a given patient. This line or reference is referred to as the orbitomeatal line (16). The orbitomeatal line (16) extends from the orbital ridge (12) to the center point of the external auditory meatus (14) on each side of the head (11). These first and second orbitomeatal lines (16) are localization base lines.

Figure 5:
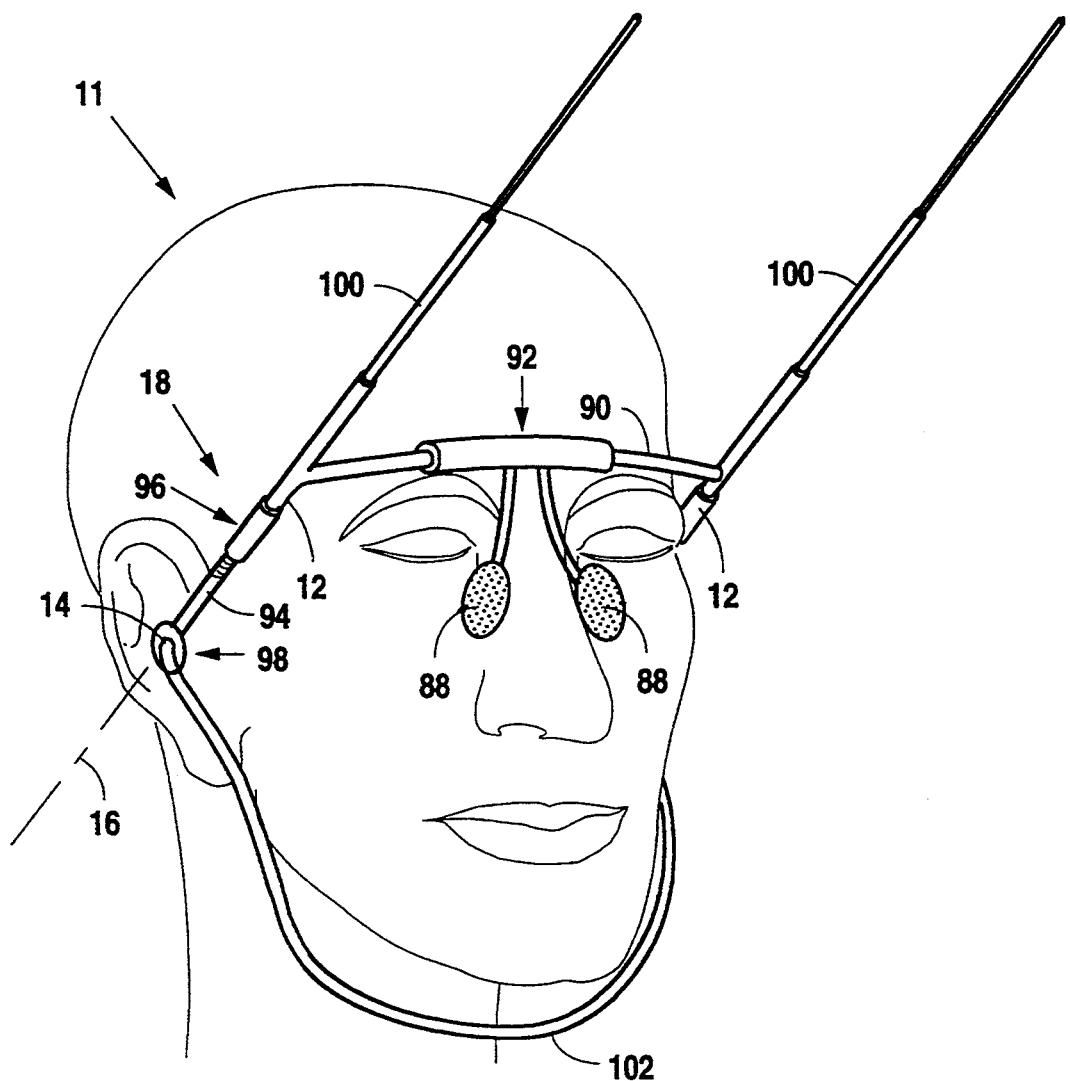
FIG. 5 is a front perspective view of the localization frames as used for establishing and aligning locations of natural references.
Figure 6:
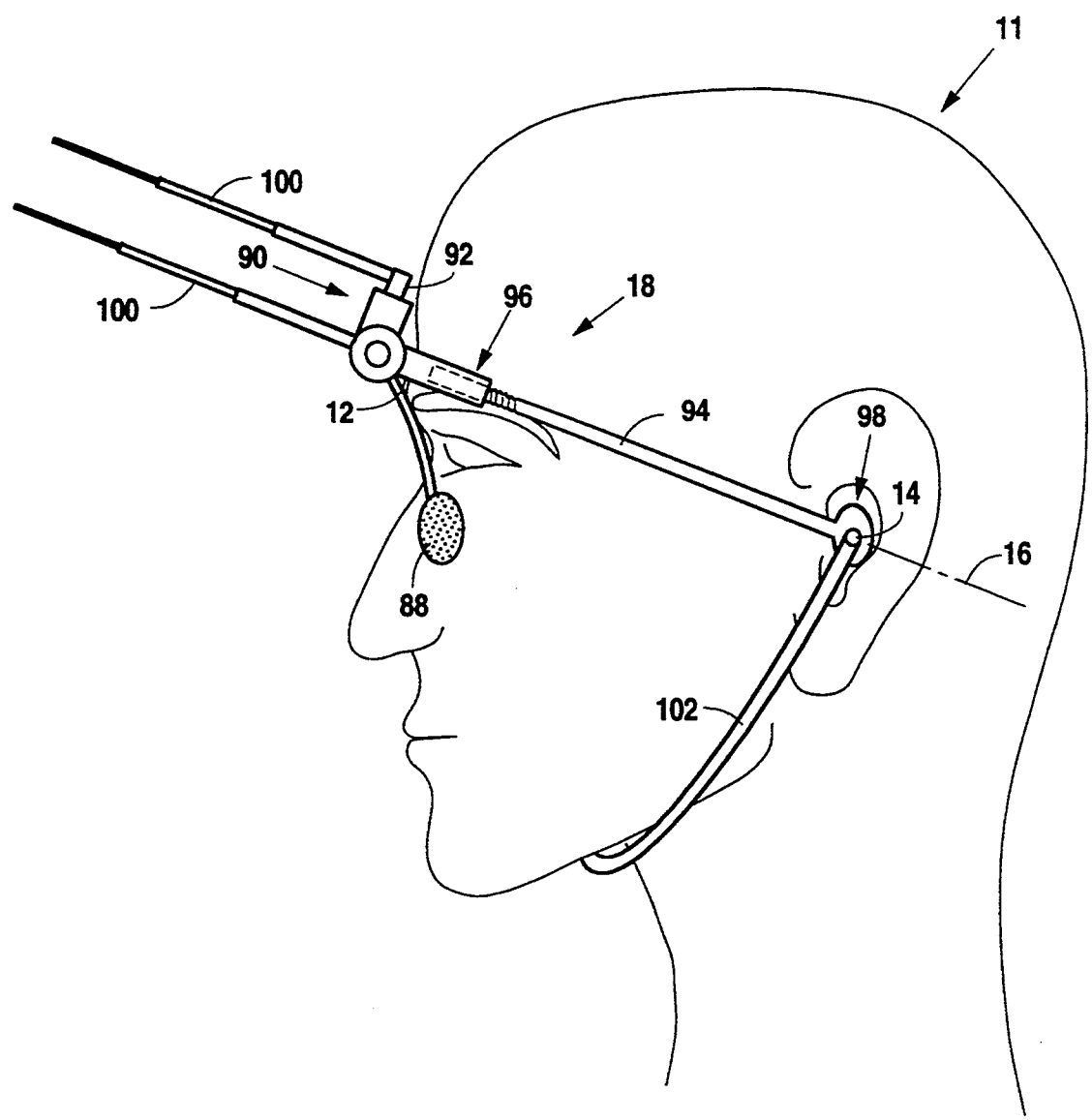
FIG. 6 is a side view of the localization frames as used for establishing and aligning locations of natural references.

Applicant's invention employs localization frames (18) which when worn, overlie the orbitomeatal line (16) on each side of the head (11). Referring to FIGS. 5 and 6, Applicant's localization frames (18) appear in more detail. These frames, supported by a nose piece (88), rest on and across the bridge of the patient's nose. A substantially horizontal arm (90), attached to the nose piece (88), extends across the patient's forehead between the patient's first and the second orbital ridges (12). For appropriate alignment and fit, an adjustment means (92) on the horizontal arm (90), such as a screw adjustment, rack and pinion connection, or spring tensioned adjustable joint, permits adjustment of the frames' (18) width. In addition, a vertical adjustment means on the nose piece (88) permits vertical adjustment to the length of the nose piece.

Connected to each end of the horizontal arm (90) and extending to the external auditory meatus (14) on each side of the head (11) are side members (94). Each side member (94) overlies or traces the orbitomeatal line (16) from the orbital ridge (12) to the external auditory meatus (14) on the corresponding side of the patient's head (11). For adjusting the length of each side member (94), an adjustment means (96), such as a screw adjustment, rack and pinion connection, or spring tensioned adjustable joint, connects the side member (94) to the corresponding end of the horizontal arm (90). Ear plugs (98) establish the central axis endpoints and position the side member (94) between the orbital ridge (12) and the external auditory meatus (14). Telescoping members (100) perpendicularly projecting from the horizontal arm (90) in line with each side member (94), may then be utilized to extend and further visualize the orbitomeatal reference line (16).

The localization frames (18), although supported on the patient's head (11), must remain still for accurate establishment of reference lines and planes. Still and secure placement of the localization frames (18) is effectuated through a spring biased U-shaped band (102) which extends under the patient's chin and is connected to the ear plugs (98). This U-shaped band (102) ensures secure placement but allows for easy positioning and removal of the glasses (18).

Referring once again to FIG. 1, these orbitomeatal lines (16) show up on an x-ray for establishing an accurate localization base. Thereafter, any time the frames (18) are removed and subsequently reworn, they should overlie the same lines on the skull. Proper placement can be checked with an x-ray by ensuring that the x-ray beams are parallel to the orbitomeatal lines. If the x-ray beams reveal a tilt, then the first and second orbitomeatal lines are off and it is known that the first and second orbitomeatal lines are not parallel.

Figure 3:
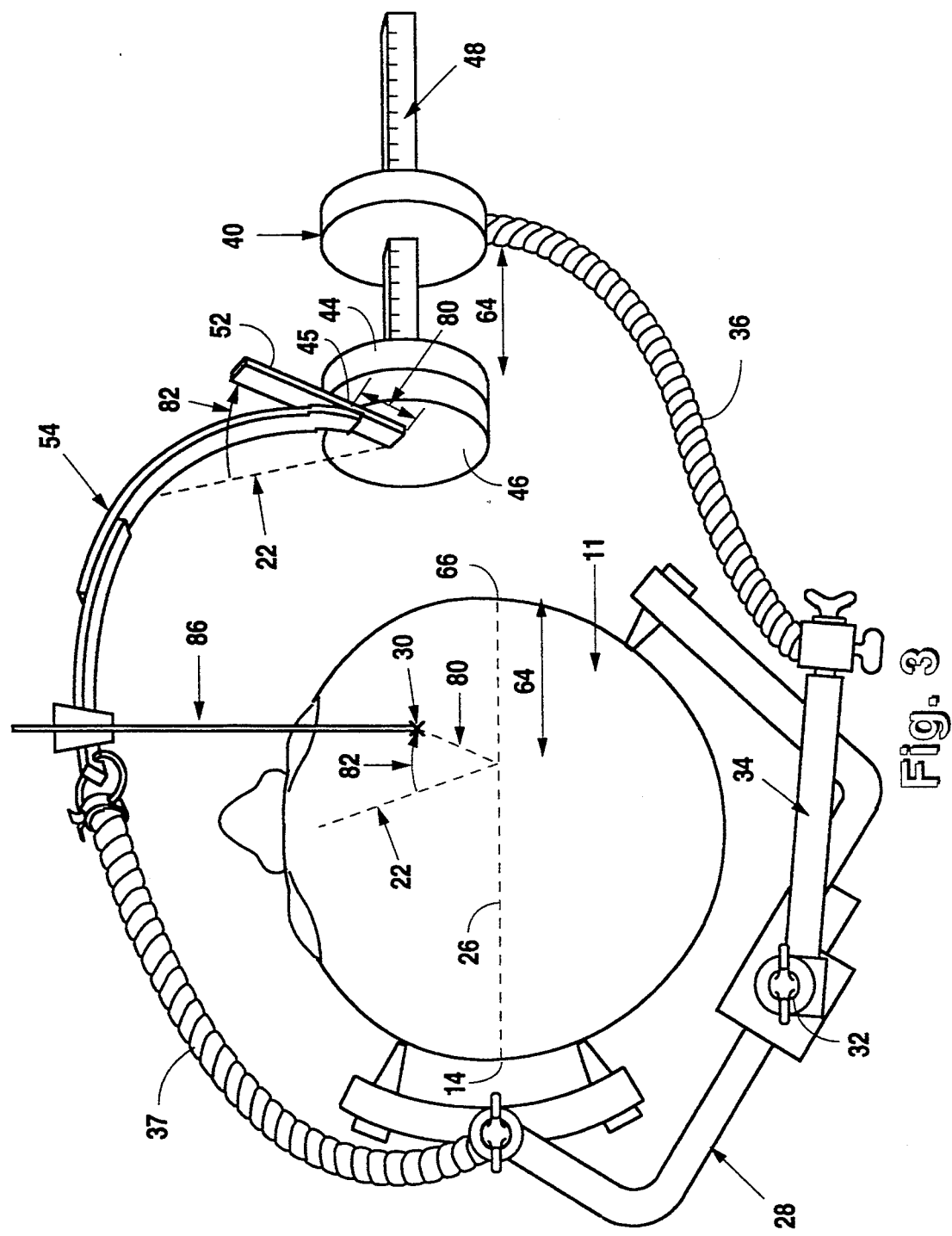
FIG. 3 is a top view of Applicant's invention as used for localization of a target point within a patient's head.

Connecting the center points of the external auditory meatii (14) with an imaginary line establishes a reference called the central axis (26) (See FIG. 3). By connecting the first and second orbitomeatal lines, an orbitomeatal plane (22) is formed. Ninety degrees to the orbitomeatal plane is the vertical plane (24) which intersects the orbitomeatal plane (22) at ninety degrees along the central axis (26). By making reference to the central axis (26), the orbitomeatal plane (22), and the vertical plane (24), localization of any point within the brain is possible. This method of stereotactic localization is based on the 360 degrees of potential rotation around this central axis (26).

After all of the cranial references are established, the stereotactic frame (10) is attached to a head frame (28) (See FIG. 3). The head frame (28), preferably a Mayfield head frame, supports the patient's head (11) and is used for most brain operations. Applicant aligns the stereotactic frame (10) such that its' horizontal arm (42) and vertical arm (not shown), at 0 and 90 degrees, are parallel to the orbitomeatal plane (22) and vertical plane (24). Once the stereotactic frame (10) is aligned, further adjustments are made.

In attaching the stereotactic frame (10), a fixed mount member (32) secures the stereotactic frame (10) to a head frame (28). The stereotactic frame (10) may be attached to a head frame (28) such that whenever the head (11) is moved the entire stereotactic frame (10) moves accordingly without any disproportionate movement between the head (11) and the stereotactic frame (10).

An edged piston member (34) is in it's non-extended position while aligning the stereotactic frame (10). After aligning the stereotactic frame (10), however, the edged piston member (34) enables movement of the stereotactic frame (10) away from the surgery field. This edged piston member (34) gives the surgeon an extra five to six inches of room since the entire stereotactic frame (10) may be moved away from the head (11). When needed, the stereotactic frame (10) is pushed back such that the edged piston member (34) is once again in its' non-extended position. The stereotactic frame (10) is accordingly returned to its' original placement wherein all reference lines remain accurate and consistent.

Applicant's preferred embodiment incorporates a locking, snake-like retractor arm (36) for positioning the stereotactic frame (10) in any required position. Positioning of the snake-like retractor arm (36) allows a third disc (46) (subsequently discussed in greater detail) to provide accessibility to any point within 360 degrees of the central axis (26). Therefore, even lesions of the posterior fossa (38) (See FIG. 2) can be easily localized without reversing the entire stereotactic frame (10).

For proper positioning of the stereotactic frame (10), the first disc (40) is positioned with its' 0 degree arm (42) and 90 degree arm (not shown) parallel to the orbitomeatal plane (22) and vertical plane (24), respectively. Positioning of the first disc (40) in this manner allows reference to the naturally occurring cranial landmarks (11). Once this position is achieved, it should not be altered. The snake-like retractor arm (36) is then locked such that the only allowable movement of the stereotactic frame (10) is movement of the entire stereotactic frame (10) away from the surgery field. A second snake-like stabilizer arm (37) may also be employed to ensure stability of the stereotactic frame (10).

The rotatably attached third disc (46) is secured to the end of an elongated rod (48). This elongated rod (48) slidably engages the first disc (40) which has a centered opening (50) allowing for movement or sliding of the elongated rod (48) through the first disc (40). The second disc (44) is attached to the elongated rod (48) such that when the second disc (44) and third disc (46) are initially slid towards the first disc (40), the second disc (44) is immediately adjacent to the first disc (40) (shown in FIG. 2). The radial arm (52) of the third disc (46) is then placed in parallel alignment with the orbitomeatal plane (22) or the vertical plane (24).

Figure 2:
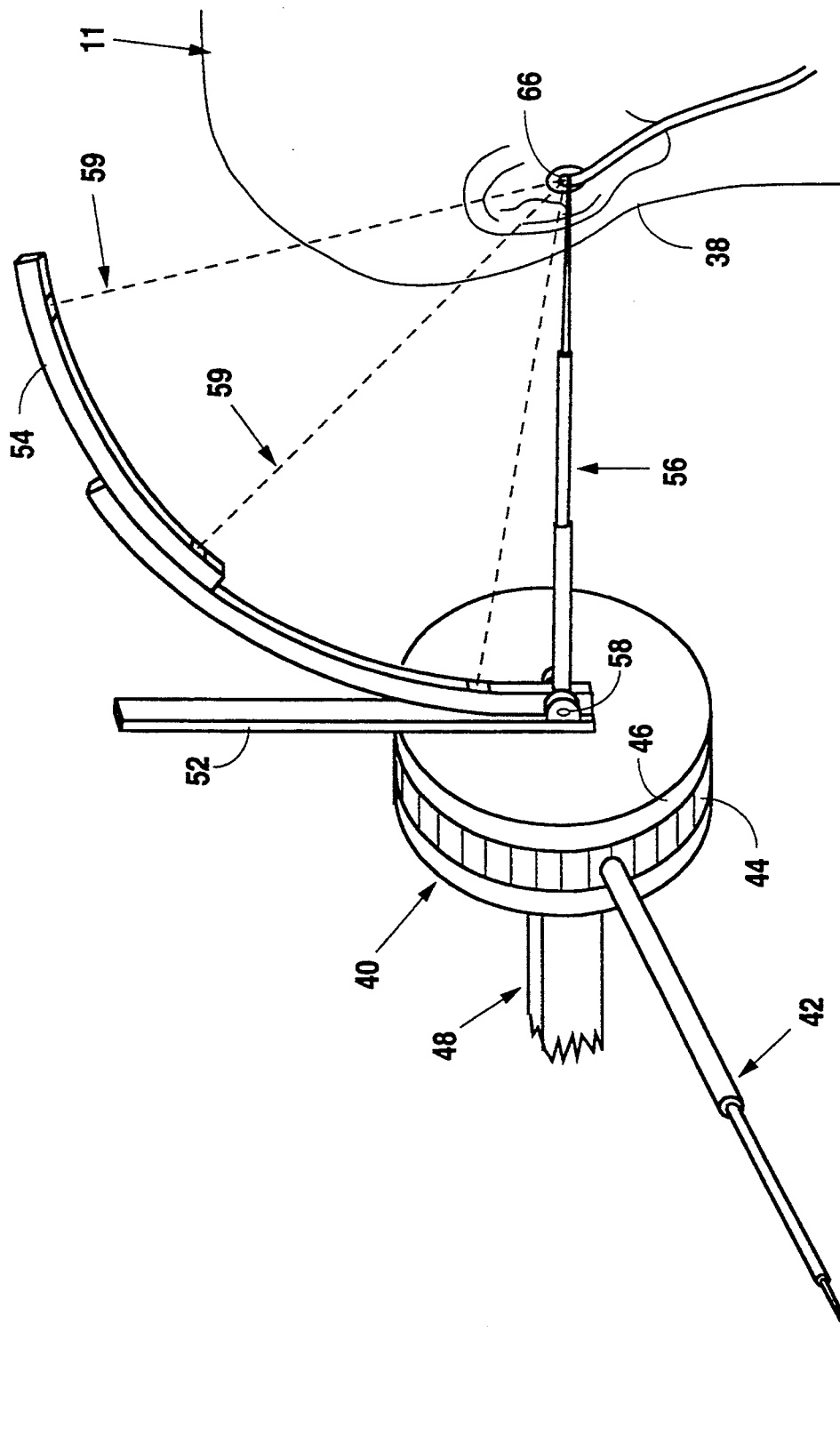
FIG. 2 is a partial side view of Applicant's stereotactic frame in its' initial alignment position.

Referring to FIG. 2, an arc frame (54) provides an initial outline for an imaginary sphere. The radius of this sphere (56) is the distance from the center point of the external auditory meatus closest to the stereotactic frame (66) to the center point of the third disc (58) when the second (44) and third (46) discs are immediately adjacent to the previously aligned first disc (40). The base of the arc frame (54) should initially meet the center point of the third disc (58). Because the sphere always maintains the same radius (56), any line (59) passing perpendicularly through the arc will intersect the center of the sphere which is the target point (30). Therefore, in physically localizing the target point (30), two laser beams (20) which are perpendicularly passed through the arc intersect at the target point (30).

The arc frame (54) is telescoping such that the radius of the sphere (56) meets at the same point whether the arc frame (54) is retracted or elongated. Therefore, at the time of initial positioning, since the base of the arc frame (54) meets the center point of the third disc (58), any line (59) passing perpendicularly through the arc will intersect the center point of the closest auditory meatus (66).

Figure 4:
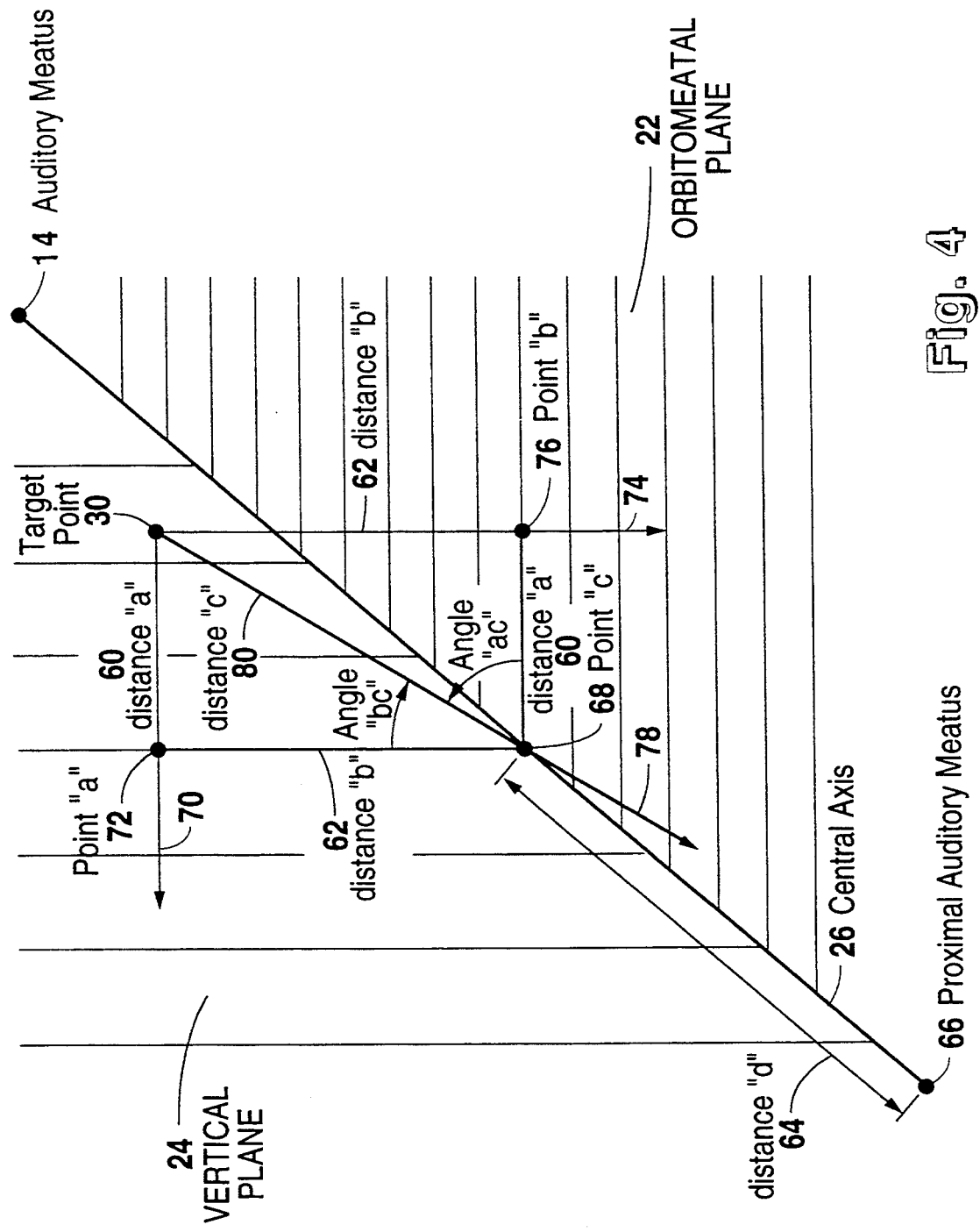
FIG. 4 is a three-dimensional graphical representation of Applicant's variable determination with respect to a patient's natural references.

Referring now to FIG. 4, in order to localize the target point (30), the value for three variables is initially required: (A) the distance a(60) from the central axis (26) to the target point (30) taken along the orbitomeatal plane (22) or a plane parallel to the orbitomeatal plane; (B) the distance b(62) from the central axis (26) to the target point (30) taken along the vertical plane (24) or a plane parallel to the vertical plane; and (C) the distance (64) from the center point of the closest external auditory meatus (66) to the point on the central axis (68) closest to the target point (30) taken along the central axis (26).

In order to determine the value for the above-mentioned variables, a line "a" (70) is projected from the target point (30) to a closest point "a" (72) on the vertical plane (24). Distance "a" (60), the desired value, is therefore the distance from the target point (30) to point "a" (72). Distance "b" (62) is equal to the distance between point "a" (72) and the central axis (26) taken along the vertical plane (24).

Alternatively, distance "b" (62) can be determined by projecting a line "b" (74) from the target point (30) to the closest point on the orbitomeatal plane, point "b" (76). Distance "b" (62) is the distance from the target point (30) to the orbitomeatal plane (22), taken along line "b" (74). Distance "a" (60) is equal to the distance from point "b" (76) to the central axis (26) taken along the orbitomeatal plane (22).

A line "c" (78) is also projected through the target point (30) to the closest point on the central axis, point "c" (68). Distance "d" (64), the third required variable, is the distance from the center point of the closest external auditory meatus (66) to point "c" (68).

Determination of other needed values is achieved through calculations using distance "a" (60), distance "b" (62), and distance "d" (64). Distance "c" (80), the distance from the target point (30) to point "c" (68), is determined through use of the Pythagorean theorem, $a^2+b^2=c^2$, with a=distance "a" (60) and b=distance "b" (62).

In addition:
$$\text{Angle "ac"} = \text{inv sin } b/c$$
$$\text{or}$$
$$= \cos a/c$$
$$\text{Angle "bc"} = \text{inv sin } a/c$$
$$\text{or}$$
$$= \text{inv cos } b/c$$

Where:
Angle "ac" = the angle between lin "a" (70) and line "c" (78);
Angle "bc" = the angle between line "b" (74) and line "c" (78);
a = distance "a"; and
b = distance "b".

Therefore, in order to locate the target point (30), the second disc (44) is moved away from the first disc (40) by the previously determined distance "d" (64). The radial arm (52) of the third disc (46) is then rotated through the angle "ac" (82) if the orbitomeatal plane (22) is the 0 degree reference plane or through an angle "bc" (84) if the vertical plane (24) is the 0 degree reference plane. The arc frame (54) is then slid along the radial arm (52) by a distance "c" (80). In this position, any projection, such as a needle guide (86), which is perpendicularly inserted through the arc frame (54) will pass through the target point (30) at the radius distance (56) from the arc frame (54).

The depth of the target point (30) then dictates further surgical procedure. If the target point (30) is deep within the brain, the stereotactic frame (10) remains locked in position throughout the procedure such that the needle guide (86) can be used for processes including biopsies or fluid draining. Alternatively, if the target point (30) is on or near the surface of the brain, the needle guide (86) is used primarily to localize the target point (30). The stereotactic frame (10) and needle guide (86) are then slid away from the surgery field such that the appropriate section of the skull can be removed and the process continued.

What is claimed is:

1. A method of stereotactic localization of a target point in a patient's head comprising the steps of:
   a. establishing a first orbitomeatal line on a first side of a patient's head, said first orbitomeatal line extending from a first orbital ridge to a center point of a first external auditory meatus;
   b. establishing a second orbitomeatal line on a second side of said patient's head, said second orbitomeatal line extending from a second orbital ridge to a center point of a second external auditory meatus;
   c. establishing an orbitomeatal plane, said orbitomeatal plane formed by connecting said first orbitomeatal line and said second orbitomeatal line;
   d. establishing a central axis in said orbitomeatal plane, said central axis formed by connecting said center points of said first external auditory meatus and said second external auditory meatus;
   e. establishing a vertical plane perpendicularly intersecting said orbitomeatal plane along said central axis;
   f. using said orbitomeatal plane, said vertical plane, and said central axis to form a spherical coordinate system to locate said target point in said patient's head.

2. A method of stereotactic localization of a target point in a patient's head as recited in claim 1 further comprising taking electronic image slices of said patient's head and of said target point, and transferring said target point location into said spherical coordinate system.

3. A method of stereotactic localization of a target point in a patient's head as recited in claim 2 comprising the steps of:
   a. supporting said patient's head in a head frame;
   b. attaching a stereotactic frame to said head frame; and
   c. using said stereotactic frame to position a needle guide proximate to said target point.

4. A method of stereotactic localization as recited in claim 3 comprising the steps of:
   a. removably fastening a fixed mount member of said stereotactic frame to said head frame, said fixed mount member including a rigidly attached bar;
   b. locking a snake-like retractor arm of said stereotactic frame in a desired configuration;
   c. positioning a first disc, affixed to an end of said snake-like retractor arm, such that said first disc aligns with said patient's head, said first disc having a centered opening, a zero degree arm, and a ninety degree arm; and
   d. positioning a second disc and a third disc in relation to said patient's head wherein said second disc and said third disc are rotatably attached, said second disc and said third disc further secured to a first end of an elongated rod wherein said elongated rod slidably engages said first disc.

5. A method of stereotactic localization as recited in claim 4, wherein positioning said first disc in relation to said patient's head comprises the steps of:
   a. aligning said 0 degree arm of said first disc with said orbitomeatal plane; and
   b. aligning said 90 degree arm of said first disc with said vertical plane.

6. A method of stereotactic localization as recited in claim 4, wherein positioning said first disc in relation to said patient's head comprises the steps of:
   a. aligning said 0 degree arm of said first disc with said vertical plane; and
   b. aligning said 90 degree arm of said first disc with said orbitomeatal plane.

7. A method of stereotactic localization as recited in claim 4, wherein positioning said second disc and said third disc comprises the steps of:
   a. sliding said second disc and said third disc towards said first disc such that said second disc is immediately adjacent to said first disc;
   b. aligning a radial arm, attached to said third disc, with said orbitomeatal plane;
   c. positioning an arc frame, slidably attached to said radial arm, such that a base of said arc frame meets a center point of said third disc; and
   d. establishing a radius distance "r" wherein said radius distance "r" is the distance from said center point of said third disc to a closest one of said first auditory meatus and said second auditory meatus, said radius distance "r" being a radius of said arc frame.

8. A method of stereotactic localization as recited in claim 7 further comprising the steps of:
   a. determining a distance "a" from said central axis to said target point in a plane "a" wherein said plane "a" is parallel with said orbitomeatal plane;
   b. determining a distance "b" from said central axis to said target point in a plane "b" wherein said plane "b" is parallel with said vertical plane;
   c. determining a point "c" on said central axis by projecting a line "c" from said target point to a closest point on said central axis; and
   d. determining a distance "d" along said central axis, said distance "d" being a shorter distance from said point "c" to either said first auditory meatus or said second auditory meatus.

9. A method of stereotactic localization as recited in claim 8, wherein determining said distance "a" comprises the steps of:
   a. projecting a line "a" from said target point to a closest point "a" on said vertical plane;
   b. ascertaining said distance "a" from said target point to said vertical plane along said line "a".

10. A method of stereotactic localization as recited in claim 9 further comprises the step of calculating an angle "ac" between said line "a" and said line "c".

11. A method of stereotactic localization as recited in claim 10 further comprising the steps of:
    a. moving said second disc and said third disc away from said first disc by said distance "d";
    b. rotating said third disc through said angle "ac" from said orbitomeatal plane;
    c. sliding said arc frame along said radial arm by said distance "c"; and
    d. inserting a needle guide through said arc frame at a point of insertion wherein said needle guide is perpendicular to said arc frame at said point of insertion, said needle guide passing through said target point at a distance "r" from said arc frame.

12. A method of stereotactic localization as recited in claim 8, wherein determining said distance "b" comprises the steps of:
    a. projecting a line "b" from said target point to a closet point "b" on said orbitomeatal plane;

b. ascertaining said distance "b" from said target point to said orbitomeatal plane along said line "b".

13. A method of stereotactic localization as recited in claim 12 further comprises the step of calculating an angle "bc" between said line "b" and said line "c".

14. A method of stereotactic localization as recited in claim 13 further comprising the steps of:
   a. moving said second disc and said third disc away from said first disc by said distance "d";
   b. rotating said third disc through said angle "bc" from said vertical plane;
   c. sliding said arc frame along said radial arm by said distance "c"; and
   d. inserting a needle guide through said arc frame at a point of insertion wherein said needle guide is perpendicular to said arc frame at said point of insertion, said needle guide passing through said target point at a distance "r" from said arc frame.

15. A method of stereotactic localization as recited in claim 14 wherein said rigidly attached bar is an edged piston member, further comprising the step of extending said edged piston member to an elongated position for removing said sterotactic frame from the surgery field after locating said target point.

16. A method of stereotactic localization as recited in claim 4, wherein positioning said second disc and said third disc comprises the steps of:
   a. sliding said second disc and said third disc towards said first disc such that said second disc is immediately adjacent to said first disc;
   b. aligning a radial arm, attached to said third disc, with said vertical plane;
   c. positioning an arc frame, slidably attached to said radial arm, such that a base of said arc frame meets a center point of said third disc; and
   d. establishing a radius distance "r" wherein said radius distance "r" is the distance from said center point of said third disc to a closest one of said first auditory meatus and said second auditory meatus, said radius distance "r" being the radius of said arc frame.

17. A method of stereotactic localization of a target point in a patient's head, said patient's head supported by a head frame during surgery, comprising the steps of:
   a. positioning a localization frame on a patient's head such that a first side member of said localization frame establishes a first orbitomeatal line on a first side of said patient's head, said first orbitomeatal line extending from a first orbital ridge to a center point of a first external auditory meatus and a second side member of said localization frame establishes a second orbitomeatal line on a second side of said patient's head, said second orbitomeatal line extending from a second orbital ridge to a center point of a second external auditory meatus;
   b. establishing an orbitomeatal plane by connecting said first orbitomeatal line and said second orbitomeatal line;
   c. establishing a central axis in said orbitomeatal plane by connecting said center points of said first external auditory meatus and said second external auditory meatus;
   d. establishing a vertical plane perpendicularly intersecting said orbitomeatal plane along said central axis;
   e. attaching a stereotactic frame to said head frame;
   f. determining variable values for location of a target point within said patient's head; and
   g. locating said target point.

18. A method of stereotactic localization of a target point in a patient's head, said patient's head supported by a head frame during surgery, as recited in claim 17 further comprising the step of using said stereotactic frame to position a needle guide proximate to said target point.

19. A method of stereotactic localization as recited in claim 17 further comprising the steps of:
   a. removably fastening a fixed mount member of said stereotactic frame to said head frame for securing said stereotactic frame to said head frame;
   b. stationing an edged piston member, said edged piston member attached to said fixed mount member;
   c. locking a snake-like retractor arm of said stereotactic frame in a desired configuration;
   d. positioning a first disc, affixed to an end of said snake-like retractor arm, such that said first disc aligns with said patient's head, said first disc having a centered opening, a zero degree arm, and a ninety degree arm; and
   e. positioning a second disc and a third disc in relation to said patient's head wherein said second disc and said third disc are rotatably attached, said second disc and said third disc further secured to a first end of an elongated rod wherein said elongated rod slidably engages said first disc.

20. A method of stereotactic localization as recited in claim 19, wherein positioning said first disc in relation to said patient's head comprises the steps of:
   a. aligning said 0 degree arm of said first disc with said orbitomeatal plane; and
   b. aligning said 90 degree arm of said first disc with said vertical plane.

21. A method of stereotactic localization as recited in claim 19, wherein positioning said first disc in relation to said patient's head comprises the steps of:
   a. aligning said 0 degree arm of said first disc with said vertical plane; and
   b. aligning said 90 degree arm of said first disc with said orbitomeatal plane.

22. A method of stereotactic localization as recited in claim 19, wherein positioning said second disc and said third disc comprises the steps of:
   a. sliding said second disc and said third disc towards said first disc such that said second disc is immediately adjacent to said first disc;
   b. aligning a radial arm, attached to said third disc, with said orbitomeatal plane;
   c. positioning an arc frame, slidably attached to said radial arm, such that a base of said arc frame meets a center point of said third disc; and
   d. establishing a radius distance "r" wherein said radius distance "r" is the distance from said center point of said third disc to a closest one of said first auditory meatus and said second auditory meatus, said radius distance "r" being the radius of said arc frame.

23. A method of stereotactic localization as recited in claim 19, wherein positioning said second disc and said third disc comprises the steps of:
   a. sliding said second disc and said third disc towards said first disc such that said second disc is immediately adjacent to said first disc;
   b. aligning a radial arm, attached to said third disc, with said vertical plane;

c. positioning an arc frame, slidably attached to said radial arm, such that a base of said arc frame meets a center point of said third disc; and d. establishing a radius distance "r" wherein said radius distance "r" is the distance from said center point of said third disc to a closest one of said first auditory meatus and said second auditory meatus, said radius distance "r" being the radius of said arc frame.

24. A method of stereotactic localization as recited in claim 19 further comprising the step of extending said edged piston member to an elongated position for removing said stereotactic frame from the surgery field after locating said target point.

25. A method of stereotactic localization as recited in claim 17 wherein determining said variable values comprises the steps of:

a. determining a distance "a" from said central axis to said target point in a plane "a" wherein said plane "a" is parallel with said orbitomeatal plane;

b. determining a distance "b" from said central axis to said target point in a plane "b" wherein said plane "b" is parallel to said vertical plane;

c. determining a point "c" on said central axis by projecting a line "c" from said target point to a closest point on said central axis; and d. determining a distance "d" along said central axis, said distance "d" being a shorter distance from said point "c" to either said first auditory meatus or said second auditory meatus.

26. A method of stereotactic localization as recited in claim 25, wherein determining said distance "a" comprises the steps of:

a. projecting a line "a" from said target point to a closest point "a" on said vertical plane; and b. ascertaining said distance "a" from said target point to said vertical plane along said line "a".

27. A method of stereotactic localization as recited in claim 26 wherein determining said variable values further comprises the step of calculating an angle "ac" between said line "a" and said line "c".

28. A method of stereotactic localization as recited in claim 27, wherein locating said target point comprises the steps of:

a. moving said second disc and said third disc away from said first disc by said distance "d";

b. rotating said third disc through said angle "ac" from said orbitomeatal plane;

c. sliding said arc frame along said radial arm by said distance "c"; and d. inserting a needle guide through said arc frame at a point of insertion wherein said needle guide is perpendicular to said arc frame at said point of insertion, said needle guide passing through said target point at a distance "r" from said arc frame.

29. A method of stereotactic localization as recited in claim 25, wherein determining said distance "b" comprises the steps of:

a. projecting a line "b" from said target point to a closest point "b" on said orbitomeatal plane; and b. ascertaining said distance "b" from said target point to said orbitomeatal plane along said line "b".

30. A method of stereotactic localization as recited in claim 29 wherein determining said variable values further comprises the steps of calculating an angle "bc" between said line "b" and said line "c".

31. A method of stereotactic localization as recited in claim 30, wherein locating said target point comprises the steps of:

a. moving said second disc and said third disc away from said first disc by said distance "d";

b. rotating said third disc through said angle "bc" from said vertical plane;

c. sliding said arc frame along said radial arm by said distance "c"; and d. inserting a needle guide through said arc frame at a point of insertion wherein said needle guide is perpendicular to said arc frame at said point of insertion, said needle guide passing through said target point at a distance "r" from said arc frame.

* * * * *